United States Patent [19]

Brewster et al.

[11] Patent Number: 4,908,380

[45] Date of Patent: Mar. 13, 1990

[54] PHARMACEUTICAL COMPOSITIONS

[75] Inventors: Andrew G. Brewster, Macclesfield; George R. Brown, Wilmslow; Michael J. Smithers, Macclesfield, all of United Kingdom

[73] Assignee: Imperial Chemical Industries plc, London, England

[21] Appl. No.: 118,226

[22] Filed: Nov. 3, 1987

[30] Foreign Application Priority Data

Nov. 4, 1986 [GB] United Kingdom ................ 8626297

[51] Int. Cl.$^4$ ........................................... A61K 31/075
[52] U.S. Cl. ..................................... 514/452; 549/369
[58] Field of Search ................ 514/452; 568/611, 593, 568/583; 549/369

[56] References Cited

FOREIGN PATENT DOCUMENTS 0256805 8/1987 European Pat. Off. .
2111050 6/1983 United Kingdom .

OTHER PUBLICATIONS

J. Med. Chem., 1985, 28, 1427–1432; Cross et al.
J. Med. Chem., 1986, 29, 1461–1468; Johnson et al.
J. Med. Chem., 1986, 29, 342–346; Cross et al.
Br. J. Pharmac., 1985, 86, 497–504, Ambler et al.
J. Med. Chem., 1985, 28, 164–170, Ford et al.
J. Med. Chem., 1981, 24, 1139–1148, Iizuka et al.
Journal of Medicinal Chemistry, 1981, vol. 24, No. 10; 1149–1155; Tanouchi et al.
J. Med. Chem., 1985, 28, 287–294; Kato et al.
J. Med. Chem., 1986, 29, 523–530, Wright et al.
Antihypertensive Drugs, (4410–4415).
Arzneim.-Forsch/Drug Res., 36(I), No. 1, (1986), Sincholle et al.
J. Med. Chem., 1987, 30, 1812–1818; Manley et al.
Thromb Haemostas, (Stuttgart), 52 (3), 364, (1984).

*Primary Examiner*—Amelia Burgess Yarbrough
*Attorney, Agent, or Firm*—Cushman, Darby & Cushman

[57] ABSTRACT

The invention concerns novel pharmaceutical compositions containing a 4(Z)-6-(2,4-diphenyl-1,3-dioxan-5-yl)-alkenoic acid which antagonizes one or more of the actions of thromboxane $A_2$, together with a compound which inhibits the synthesis of thromboxane $A_2$. The compositios are useful as medicines in treating a variety of diseases or medical conditions in which thromboxane $A_2$ and/or other prostanoid contractile substances are involved.

14 Claims, No Drawings

PHARMACEUTICAL COMPOSITIONS

This invention concerns novel pharmaceutical compositions and, more particularly, novel pharmaceutical compositions comprising a 4-(Z)-6-([2,4,5-cis]-2,4-diphenyl-1,3-dioxan-5-yl)-hexenoic acid which antagonises one or more of the actions of thromboxane $A_2$ (hereafter referred to as "$TXA_2$") together with a compound which inhibits the synthetase of $TXA_2$ (hereafter referred to as a $TXA_2$ synthetase inhibitor). Such compounds are of value as therapeutic agents.

It is known that the arachidonic acid metabolite thromboxane $A_2$ is a powerful vasoconstrictor and a potent aggregator of blood platelets. $TXA_2$ is also a potent constrictor of bronchial and tracheal smooth muscle. $TXA_2$ is believed to be involved in a variety of diseases and medical conditions, for example, ischaemic heart disease (such as myocardial infarction), angina, cerebrovascular disease (such as transient cerebral ischaemia, migraine and stroke), peripheral vascular disease (such as atherosclerosis, microangiopathy), hypertension and in blood clotting defects due to lipid imbalance.

It is believed that $TXA_2$ exerts its physiological action through the thromboxane receptor, at which receptor various other prostanoid contractile substances derived from arachidonic acid, such as prostaglandins $H_2$, $F_2$ alpha and prostaglandin $D_2$, can exert contractile effects. There are two principal ways in which the effects of $TXA_2$ (and also of prostaglandins $H_2$, $F_2$ alpha and/or $D_2$) can be ameliorated. The first is by administering a pharmacological agent which preferentially occupies the thromboxane receptor, but yet does not produce the contractile effects which follow the binding of $TXA_2$ (or of prostaglandins $H_2$, $F_2$ alpha and/or $D_2$). Such an agent is said to possess $TXA_2$ antagonist properties. The second way is to administer a pharmacological agent which inhibits one or more of the enzymes involved in the production of $TXA_2$ and in particular, which inhibits the enzyme known as thromboxane synthetase ($TXA_2$ synthetase). Such an agent is said to be a $TXA_2$ synthetase inhibitor.

Accordingly, compositions which contain active ingredients which antagonise the actions of $TXA_2$ and which inhibit the production of $TXA_2$ may be expected to have therapeutic value in the prevention or treatment of any one or more of the above mentioned diseases or any other medical conditions in which $TXA_2$ and/or prostaglandins $H_2$, $F_2$ alpha and/or $D_2$ are involved, including asthmatic and inflammatory diseases. We have now discovered that particularly useful $TXA_2$ antagonism is shown by a novel group of 2,4-diphenyl-1,3-dioxanes of formula I below and that it is particularly advantageous to incorporate such a novel compound together with a $TXA_2$ synthetase inhibitor into a pharmaceutical composition, and this is the basis for our invention.

According to the invention there is provided a pharmaceutical composition comprising as active ingredients:

(i), a novel 2,4-diphenyl-1,3-dioxane of the formula I (set out hereinafter) wherein X is selected from fluoro, chloro, bromo, trifluoromethyl, cyano, methoxy and nitro; and one of Y and Z is hydrogen or fluoro, and the other is hydrogen; and wherein the groups at positions 2, 4 and 5 of the dioxane ring have cis-relative stereochemistry; or a pharmaceutically acceptable salt thereof; and (ii) an inhibitor of the synthesis of thromboxane $A_2$ (hereinafter referred to as a $TXA_2$ synthetase inhibitor); together with a pharmaceutically acceptable diluent or carrier.

It will be appreciated that the compounds of formula I possess asymmetric carbon atoms and may exist and be isolated in racemic and optically active forms. The active ingredient (i) can be a racemic form or any optically active form (or mixtures thereof) which is capable of antagonising one or more of the actions of $TXA_2$, it being well known in the art how to prepare individual optical isomers (for example by synthesis from optically active starting materials or resolution of a racemic form) and how to determine the $TXA_2$ antagonist properties using one or more of the standard tests referred to hereafter.

In the chemical formulae attached hereto, although a particular configuration is shown, this does not necessarily correspond to the absolute configuration.

Specific values for the phenyl moiety bearing X which are of particular interest include, for example, 2-fluoro-, 2-chloro-, 2-bromo-, 2-cyano-, 2-trifluoromethyl-, 3-fluoro-, 3-chloro-, 3-cyano-, 3-nitro-, 3-methoxy-, 4-chloro-, 4-cyano-, 4-nitro-and 4-methoxy-phenyl.

A preferred value for Y is hydrogen or fluoro and for Z is hydrogen.

A preferred group of active ingredients (i) comprises those compounds of the formula II wherein $X^1$ is selected from 2-chloro, 3-chloro, 2-cyano, 4-cyano, 3-nitro and 4-nitro; and the groups at positions 2, 4 and 5 of the dioxane ring have cis-relative stereochemistry; together with the pharmaceutically acceptable salts thereof.

Specific compounds of formula I of particular interest as active ingredient (i) are set out in the accompanying Examples. Of these the compounds described in Examples 1, 2, 3, 13, 14, 15 and 20 are preferred, and those in Examples 1, 2 and 13 are most preferred, together with pharmaceutically acceptable salts thereof.

Particular pharmaceutically acceptable salts of acids of formula I are, for example, alkali metal and alkaline earth metal salts such as lithium, sodium potassium, magnesium and calcium salts, aluminium and ammonium salts, and salts with organic amines and quaternary bases forming physiologically acceptable cations such as salts with methylamine, dimethylamine, trimethylamine, ethylenediamine, piperidine, morpholine, pyrrolidine, piperazine, ethanolamine, triethanolamine, N-methylglucamine, tetramethylammonium hydroxide and benzyltrimethylammonium hydroxide.

Suitable $TXA_2$ synthetase inhibitors for inclusion as active ingredient (ii) in the compositions according to the invention include, for example, the known compounds:

(1) dazoxiben (R. P. Dickinson, *J.Med.Chem.*, 1985, 28, 1427–1432);

(2) furegrelate [U63557] (R. A. Johnson, *J.Med.Chem.*, 1986, 29, 1461–1468).

(3) UK 38485 (R. P. Dickinson, *J.Med.Chem.*, 1986, 29, 342–346);

(4) CGS 12970 (J. Ambler, *Brit.J.Pharmacol.*, 1985, 86, 497–504);

(5) CGS 13080 (L. Browne, *J.Med.Chem.*, 1985, 28, 164–170);

(6) CGS 14854 (European Patent Appln, Publication No. 80154: Example 7);

(7) OKY 046 (K. Iizuka, *J.Med.Chem.*, 1981, 24, 1139–1148);

(8) OKY 1580 (M. Hayashi, *J.Med.Chem.*, 1981, 24, 1149–1155);

(9) OKY 1581 (M. Hayashi, *J.Med.Chem.*, 1981, 24, 1149–1555);

(10) CV 4151 (S. Terao, *J.Med.Chem*, 1985, 28, 287–294);

(11) N-[(1H-imidazol-1-yl)octyl]-4-chlorobenzamide *J.Med.Chem.*, 1986, 29, 523–530);

(12) CBS645 (D. Sincholle, *Arzneimittel Forsch.*, 1986, 36, 117–119);

(13) SC 41156 (F. G. Spokas, *Fed.Proc.*, 1986, 45, 913); and

(14) Y20811 (Y. Muramoto, Japanese J Pharmacology, 1986, 40, 178P;

or a pharmaceutically acceptable salt thereof. [Note: the structures of these $TXA_2$ synthetase inhibitors are given on the attached sheets A and B hereinafter.] However, any $TXA_2$ synthetase inhibitor which is chemically compatible with the active ingredient (i) may be used in the compositions of the invention.

Particularly suitable $TXA_2$ synthetase inhibitors include, for example, dazoxiben (1), CV4151 (10), and the pharmaceutically acceptable salts thereof.

The compounds of formula I may be manufactured by conventional procedures of organic chemistry well known in the art for the manufacture of structurally analogous compounds. Such procedures are illustrated by the following processes in which X, Y and Z have any of the meanings defined hereinabove:

(a) An aldehyde of the formula III is reacted with a Wittig reagent of the formula $R^1{}_3P=CH(CH_2)_2CO_2{}^- M^+$ wherein $R^1$ is (1–6C)alkyl or aryl (especially phenyl) and $M^+$ is a cation, for example an alkali metal cation such as the lithium, sodium or potassium cation.

The process in general produces the required compounds of formula I in which the substituents adjacent to the double bond have predominantly cis-relative stereochemistry i.e. the "Z" isomer. However the process also produces analogous compounds having trans-relative stereochemistry which may be removed by a conventional procedure such as chromatography or crystallisation.

The process is conveniently performed in a suitable solvent or diluent, for example an aromatic solvent such as benzene, toluene or chlorobenzene, an ether such as 1,2-dimethoxyethane, t-butyl methyl ether, dibutyl ether or tetrahydrofuran, in dimethyl sulphoxide or tetramethylene sulphone, or in a mixture of one or more such solvents or diluents. The process is generally performed at a temperature in the range, for example, −80° C. to 40° C., but is conveniently performed at or near room temperature, for example in the range 0° to 35° C.

(b) A phenol derivative of the formula IV wherein $R^1$ is a protecting group, for example (1–6C)alkyl (such as methyl or ethyl), acyl (such as acetyl, benzoyl, methanesulphonyl or p-toluenesulphonyl), allyl, tetrahydropyran-2-yl, trimethylsilyl, is deprotected.

The deprotection conditions used depend on the nature of the protecting group $R^1$. Thus, for example, when it is methyl or ethyl the deprotection may be carried out by heating with sodium thioethoxide in a suitable solvent (such as N,N-dimethylformamide or N,N-dimethyl-3,4,5,6-tetrahydro-2(1H)-pyrimidinone) at a temperature in the range, for example, 50° to 160° C. Alternatively, an ethyl or methyl protecting group may be removed by reaction with lithium diphenylphosphide in a suitable solvent (such as tetrahydrofuran or methyl t-butyl ether) at a temperature in the range, for example, 0° to 60° C. When the protecting group is acyl it may be removed, for example, by hydrolysis in the presence of a base (such as sodium or potassium hydroxide) in a suitable aqueous solvent [such as an aqueous (1–4C)alkanol] at a temperature in the range, for example, 0° to 60° C. When the protecting group is allyl or tetrahydropyran-2-yl, it may be removed, for example, by treatment with strong acid such as trifluoroacetic acid and when it is trimethylsilyl, it may be removed, for example, by reaction with aqueous tetrabutylammonium fluoride or sodium fluoride using a conventional procedure.

(c) An erythro-diol derivative of the formula V wherein one of $Q^1$ and $Q^2$ is hydrogen and the other is hydrogen or a group of the formula —$CR_aR_b$.OH (wherein $R_a$ and $R_b$ are the same or different (1–4C) alkyl) is reacted with a benzaldehyde derivative of the formula VI or an acetal, hemiacetal or hydrate thereof.

The benzaldehyde VI [or its hydrate, or its acetal or hemiacetal with a (1–4C)alkanol (such as methanol or ethanol)] may conveniently be present in an excess.

The reaction is generally performed in the presence of an acid catalyst such as hydrogen chloride, hydrogen bromide, sulphuric acid, phosphoric acid, methanesulphonic acid or p-toluenesulphonic acid, conveniently in the presence of a suitable solvent or diluent, such as toluene, xylene or an ether, for example tetrahydrofuran, dibutyl ether, methyl t-butyl ether or 1,2-dimethoxyethane, and at temperature in the range, for example, 0° to 80°. C.

Those starting materials of formula V wherein $Q^1$ and $Q^2$ are both hydrogen may be obtained, for example, by mild, acid catalysed, hydrolysis or alcoholysis of the dioxane ring of a compound of formula VII wherein $R_a$ and $R_b$ are both alkyl such as methyl or ethyl, obtained by an analogous procedure to process (a) herein. The hydrolysis or alcoholysis will normally be carried out at a temperature in range 10° to 80° C. using an aqueous mineral acid such as hydrochloric acid, in an alkanol (such as ethanol or 2-propanol) or an ether (such as tetrahydrofuran) as solvent.

The starting materials of formula V wherein one of $Q^1$ and $Q^2$ is hydrogen and the other is a group of the formula —$CR_aR_b$.OH are intermediates in the above-mentioned formation of the starting materials of formula V wherein $Q^1$ and $Q^2$ are both hydrogen. However, said intermediates are not normally isolated or characterised. Therefore a useful modification of process (c) comprises reacting a compound of formula VII wherein one of $R_a$ and $R_b$ is hydrogen, methyl or ethyl and the other is methyl or ethyl with an excess of a compound of the formula VI (or a hydrate, acetal or hemiacetal thereof) in the presence of an acid catalyst (such as one of those given above), conveniently at a temperature in the range, for example, 10° to 80° C. and optionally in the presence of a suitable solvent or diluent (such as one of those given above).

The starting materials for use in the above processes may be made by general procedures of organic chemistry, known for the preparation of structurally related compounds. Thus, the aldehydes of formula III may be obtained, for example, by the method shown in Scheme I. The protected phenol derivatives of formula IV may be made, for example, by using an analogous procedure to process (a) above using an aldehyde analogous to that of formula III, but wherein the phenol group has been protected with the group $R^1$, such an aldehyde being made, for example, by carrying out the procedures of Scheme I omitting the deprotection step (ii). Those of the starting materials of formula VII which are novel may be obtained using analogous procedures to those described in European patent application, publication No. 94239.

The necessary Wittig reagents may be obtained by conventional procedures, for example by treating the corresponding phosphonium halides with a strong base such as sodium hydride, lithium diisopropylamide, potassium t-butoxide or butyllithium. They are generally formed in situ just prior to carrying out the condensation process (a) above.

It will be understood that the compounds of formula I may also be obtained by other conventional procedures well known in the art, for example by base catalysed hydrolysis of the corresponding esters, amides or nitriles.

When a salt of a compound of formula I is required, it is obtained by reaction with the appropriate base affording a physiologically acceptable cation, or by any other conventional procedure.

Further, when an optically active form of a compound of formula I is required, one of the aforesaid processes may be carried out using an optically active starting material. Alternatively, the racemic form of a compound of formula I may be reacted with an optically active form of a suitable organic base, for example ephedrine, N,N,N-trimethyl(1-phenylethyl)ammonium hydroxide or 1-phenylethylamine, followed by conventional separation of the diastereoisomeric mixture of salts thus obtained, for example by fractional crystallisation from a suitable solvent, for example a (1–4C)alkanol, whereafter the optically active form of said compound of formula I may be liberated by treatment with acid using a conventional procedure, for example using an aqueous mineral acid such as dilute hydrochloric acid.

As stated earlier, the novel compounds of formula I are antagonists of one or more of the actions of $TXA_2$, for example certain of its actions on blood platelets, the vasculature and/or the lung. The antagonism may be demonstrated in one or other of the following standard tests:

(a) The rabbit aortal strip model devised by Piper and Vane (Nature, 1969, 223, 29–35) or the rat aortal strip model developed by Kennedy et alia (*Prostaglandins*, 1982, 24, 667–689), using as agonist a freshly prepared sample of $TXA_2$, generated by addition of arachidonic acid (25 μg) to citrated, platelet rich rabbit plasma (250 μl) and allowing the mixture to aggregate fully over 90 seconds before use; alternatively the $TXA_2$ mimetic agent known as U46619 (described by R. L. Jones et alia in "Chemistry, Biochemistry and Pharmacological Activity of Prostanoids" edited by S. M. Roberts and F. Scheinmann, at page 211; Pergamon Press, 1979) may be used as the agonist; and (b) a blood platelet aggregation test based on that described by Born (Nature, 1962, 194, 927–929) and involving:

(i) aggregating human, citrated, platelet-rich plasma by addition of the $TXA_2$ mimetic agent U46619 so that a dose-response curve is generated;

(ii) generating a dose-response curve for U46619 stimulated platelet aggregation in the presence of increasing amounts of test compound (generally in the range $10^{-5}$M to $10^{-10}$M); and (iii) calculating a $K_B$ value indicating potency of $TXA_2$ antagonism for the test compound, averaged over several concentrations, from the calculated 50% response value for U46619 aggregation in the presence and absence of test compound; and (c) a bronchoconstriction test involving measuring the inhibition by a test compound of the bronchoconstriction induced in the Konzett-Rossler, anaesthetised guinea-pig model (as modified by Collier and James, *Brit.J.Pharmacol.*, 1967, 30, 283–307) by intravenous administration of the $TXA_2$ mimetic agent, U46619 and involving:

(i) obtaining a cumulative dose-response curve to U46619 induced bronchoconstriction by intravenous administration of constant volumes of increasing concentrations of U46619 (0.2–4 μg/kg) in physiological saline solution and expressing bronchoconstriction as the maximum of that theoretically obtainable with no air flow to the test animal;

(ii) generating a cumulative dose-response curve to U46619 induced bronchoconstriction at 30 minute intervals for 3 hours after oral dosing of test compound; and (iii) calculating a dose-ratio for the test compound (that is the ratio of concentration of U46619 required to cause 50% bronchoconstriction in the presence and absence of test compound) indicating the potency of $TXA_2$ antagonism.

The antagonism of the effects of $TXA_2$ on the vasculature may be demonstrated, for example in rats in the following manner:

(d) Male rats (Alderley Park strain) are anaesthetised with sodium pentobarbital and blood pressure is monitored at the carotid artery. The $TXA_2$ mimetic agent U46619 is administered intravenously at 5 μg/kg via the jugular vein to produce 20–30 mm/Hg (2640–3970 pascal) increase in systolic blood pressure. The process is repeated twice to ensure adequacy of response. A test compound is then administered either intravenously (via the jugular vein) or orally (via a cannula) directly into the stomach and the animal challenged with U46619, five minutes after dosing with test compound and then successively every ten minutes until the hypertensive effect of U46619 is no longer blocked.

Further, the antagonism of the effects of $TXA_2$ in vivo may be demonstrated, for example, by assessing the effects of a test compound on the aggregation of blood platelets obtained after administration of test compound to a test animal, such as a rabbit, rat, guinea pig or dog, using standard procedures similar to that described in (a) above. However, when the aggregation of dog platelets is being studied it is necessary to use a predetermined, threshold concentration of the platelet aggregation agent adenosine diphosphate (about $0.4–1.2 \times 10^{-6}$M) together with the $TXA_2$ mimetic agent, U46619.

Using the above test procedures (a)–(c), the following representative results have been obtained with the compounds of formula II wherein (i) $X^1$ is 2-chloro, (ii) $X^1$ is 2-cyano; or (iii) $X^1$ is 4-cyano, respectively:

Test (a), $pA_2$ ($\pm 0.05$): (i), 8.02; (ii), 8.09; (iii) 7.45;

Test (b), $K_B$: (i), $2.92 \times 10^{-9}$M; (ii), $8.34 \times 10^{-10}$M; (iii) $5.49 \times 10^{-9}$ Test (c), dose ratio: (i) >1500; (ii), >32; (iii), >350; 2 hours after oral dosing at 0.05 mg/kg.

Similarly, using test procedure (d) referred to above, the following representative results were obtained on inhibition of U46619 induced hypertension with the compounds of formula II referred to above:

compound (i): >80% inhibition 1 hour after oral dose of 0.5 mg/kg;

compound (ii): >80% inhibition 1 hour after oral dose of 0.5 mg/kg;

compound (iii): >40% inhibition 1 hour after oral dose of 0.5 mg/kg.

In general, other compounds of formula I and II show similar levels of TXA$_2$ antagonist properties in one or more of the above mentioned tests e.g. test (a) pA$_2$>7.0; test (b) K$_B$: <1.0×10$^{-7}$M; test (c) dose ratio >5, 2 hours after oral dosing at 0.1 mg/kg and/or test (d), significant inhibition of U46619 induced hypertension for at least 1 hour following oral dosing at 5 mg/kg or less.

By way of comparison, the structurally closely related compounds 5(Z)-7-([2,4,5-cis]-2-o-chlorophenyl-4-phenyl-1,3-dioxan-5-yl)heptenoic acid (iv) and 5(Z)-7-([2,4,5-cis]-2-p-cyanophenyl-4-phenyl-1,3-dioxan-5-yl-heptenoic acid (v) disclosed, inter alia, in European patent application, publication No. 94239, possess significantly lower TXA$_2$ antagonist properties. Thus, for example, using test procedure (a) above, they have pA$_2$ values of 6.22 (iv) and 5.65 (v).

The above results indicate the unexpectedly superior TXA$_2$ antagonist properties possessed by the compounds of formula I and II.

The beneficial effects of combining one of the novel TXA$_2$ antagonists of formula I defined hereinabove with a TXA$_2$ synthetase inhibitor may be illustrated in vitro, for example by evaluating their effects in inhibiting arachidonic acid induced aggregation of human platelets, using standard procedures well known in the art. Thus, for example, the following results were obtained with the TXA$_2$ antagonist described hereinafter in Ex. 2, 6 and 20 (Compound A) and the TXA$_2$ synthetase inhibitor known as dazoxiben (Compound B):

| Compound | Concentration in vehicle | % Inhibition of vehicle control |
|---|---|---|
| A | 10$^{-9}$M | 2.2 ± 0.8 |
| B | 10$^{-5}$M | 4.5 ± 1.8 |
| B | 10$^{-4}$M | 32.2 ± 16.3 |
| A + B | 10$^{-9}$M 10$^{-5}$M | 89.9 ± 6.1* |

*p < 0.001 compared with compound B at 10$^{-5}$M using Student's t test

These results show that compounds A and B together exert a synergistic effect, which is illustrative of the expected beneficial effect to be obtained in vivo from co-administration of a novel TXA$_2$ antagonist of formula I with a TXA$_2$ synthetase inhibitor. Such a beneficial effect in vivo may also be demonstrated in laboratory animals, for example by reducing or preventing the adverse effects of platelet aggregation in rabbits following intravenous injection of arachidonic acid.

The invention also embraces a method of medical treatment of one or more diseases in which TXA$_2$ is and/or prostaglandins H$_2$, F$_2$ alpha and/or D$_2$ are involved which comprises administering to a warm-blooded animal a novel antagonist of the formula I, or a pharmaceutically acceptable salt thereof, as defined hereinbefore, and a TXA$_2$ synthetase inhibitor, for example as stated hereinbefore. Although it is envisaged that the antagonist and inhibitor will generally be administered at the same time and combined in a single composition, they may also be administered in separate compositions, by different routes and at different times in order to maximise the therapeutic effect.

As stated previously, the compositions of the invention may be used in the therapy or prevention of diseases or adverse conditions in warm-blooded animals in which it is desirable to antagonise one or more of the actions of TXA$_2$ and to inhibit its synthesis. In general, they will be administered for this purpose by an oral, rectal, intravenous, subcutaneous, intramuscular or inhalation route, so that a dose of the active ingredient (i) in the range, for example 0.01–15 mg/kg body weight (and, more particularly, 0.1–5 mg/kg body weight), is received up to four times per day, varying with the route of administration, the severity of the condition and the size and age of the patient under treatment.

The quantity of the TXA$_2$ synthetase inhibitor, present as active ingredient (ii) in the composition will necessarily vary with its potency as an inhibitor, but will typically be such an amount that a dose of the active ingredient (ii) in the range, for example 0.05–25 mg/kg body weight (and, more particularly, 0.5–10 mg/kg body weight) is received up to four times per day, varying with the route of administration, the severity of the condition and the size and age of the patient under treatment.

A unit dose of a composition of the invention will generally contain an amount of each of the active ingredients (i) and (ii) sufficient to provide a single dose of (i) or (ii), as specified above. However, because of the expected synergistic effects of co-administering (i) and (ii) to warm-blooded animals (including man), reduced amounts of the individual active ingredients may generally be used. A unit dose will, however, generally contain, for example, 0.5–1200 mg of active ingredient (i) together with 2.5–2000 mg of active ingredient (ii).

The compositions may be in a variety of dosage forms. For example, they may be in the form of tablets, capsules, solutions or suspensions for oral administration; in the form of a suppository for rectal administration; in the form of a sterile solution or suspension for administration by intravenous or intramuscular injection; in the form of an aerosol or a nebuliser solution or suspension, for administration by inhalation; and in the form of a powder, together with pharmaceutically acceptable inert solid diluents such as lactose, for administration by insufflation.

The compositions may be obtained by conventional procedures using pharmaceutically acceptable diluents and carriers well known in the art. Tablets and capsules for oral administration may conveniently be formed with an enteric coating, for example comprising cellulose acetate phthalate, to minimise contact of the active ingredient of formula I with stomach acids.

The compositions of the invention may also be used because of their combined TXA$_2$ antagonist and TXA$_2$ synthetase inhibitory properties in helping to maintain the viability of blood and blood vessels in warm-blooded animals (or parts thereof) under-going artificial extracorporeal circulation, for example during limb or organ transplant.

The preparation of the compounds of formula I is illustrated in the following Examples 1–30 and the compositions of the invention by the following non-limiting Example 31. In these Examples, unless otherwise stated:

(i) evaporations were carried out by rotary evaporation in vacuo;

(ii) operations were carried out at room temperature, that is in the range 18°–26° C. and under an atmosphere of an inert gas such as argon;

(iii) flash column chromatography was performed on Merck Kieselgel (Art. 9385) obtained from E. Merck, Darmstadt, W. Germany;

(iv) yields are given for illustration only and are not necessarily the maximum attainable;

(v) proton NMR spectra were normally determined at 90 or 200 MHz in CDCl$_3$ using tetramethylsilane (TMS) as an internal standard, and are expressed as chemical shifts (delta values) in parts per million relative to TMS using conventional abbreviations for designation of major peaks: s, singlet; m, multiplet; t, triplet; br, broad; d, doublet;

(vi) all end-products were isolated as racemates.

EXAMPLE 1

Sodium hydride (247 mg, 50% w/w dispersion in mineral oil) was added to a stirred suspension of 4(Z)-6-[2,4,5-cis]-2-o-cyanophenyl-4-o-methoxyphenyl-1,3-dioxan-5-yl)hexenoic acid (350 mg) in 1,3-dimethyl-3,4,5,6-tetrahydro-2(1H)-pyrimidinone (DMPU) (8 ml) at 0°–5° C. After 5 minutes ethanethiol (320 mg) was added dropwise during 3 minutes. The mixture was maintained at 0°–5° C. for 30 minutes and then heated at 90° C. for 6 hours. The cooled reaction mixture was diluted with water (40 ml) and extracted with dichloromethane (2×50 ml). The aqueous phase was acidified to pH 4 with acetic acid and extracted with diethyl ether (3×30 ml). The extracts were washed with saturated brine (2×30 ml), dried (MgSO$_4$) and evaporated. The oil obtained was purified by flash column chromatography on silica, eluting with 80:20:2 (by volume) toluene/ethyl acetate/acetic acid, to give 4(Z)-6-([2,4,5-cis]-2-o-cyanophenyl-4-o-hydroxyphenyl-1,3-dioxan-5-yl)hexenoic acid as a colourless solid (253 mg, 75%), m.p. 118°–121° C.; NMR: 1.91 (2H,m), 2.38 (4H,d), 2.85 (1H,m), 4.26 (2H,m), 5.46 (3H,m), 6.02 (1H,s), 6.86 (2H,m), 7.15 (3H,m) and 7.63 (4H,m); m/e: 393 (M+).

The starting acid was obtained as follows:

Potassium t-butoxide (12.3 g) was added over 2 minutes to a stirred suspension of (3-carboxypropyl)-triphenylphosphonium bromide (23.6 g) in tetrahydrofuran (THF) (230 ml) at 0°–5° C. The mixture was stirred at ambient temperature for 30 minutes and cooled to 0° C. before the addition of (4-o-methoxyphenyl-2,2-dimethyl-1,3-dioxan-cis-5-yl)acetaldehyde (5.9 g) during 5 minutes. The mixture was stirred for 45 minutes and water (50 ml) added. The solvent was removed by evaporation. The residue was dissolved in water (250 ml). The solution was washed with ethyl acetate (3×100 ml.) and then acidified to pH 4 with acetic acid. The liberated oil was extracted with ethyl acetate (3×100 ml). These extracts were washed with saturated brine (2×100 ml), dried (MgSO$_4$) and evaporated to given an oil. The oil was purified by flash column chromatography on silica, eluting with 80:20:1 (by volume) toluene/ethyl acetate/acetic acid, to give 4(Z)-6-(4-o-methoxyphenyl-2,2-dimethyl-1,3-dioxan-cis-5-yl)hexenoic acid (A), as a colourless solid (6.0 g, 82%), m.p. 92°–96° C.; NMR: 1.65 (8H,m), 2.35 (5H,m), 3.85 (5H,m), 5.28 (3H,m) and 7.1 (4H,m); [note after recrystallisation from ethyl acetate/hexane, material of m.p. 99°–101° C. may be obtained—see Ex. 20(i)].

o-Cyanobenzaldehyde (400 mg) and p-toluene sulphonic acid 5 mg) were added to a solution of A (668 mg) in toluene (12 ml) and the mixture heated under reflux at 100°–105° C. for 30 minutes. The cooled mixture was purified by flash column chromatography on silica, eluting with 80:20:1 (by volume) toluene/ethyl acetate/acetic acid, to give 4(Z)-6-([2,4,5-cis]-2-o-cyanophenyl-4-o-methoxyphenyl-1,3-dioxan-5-yl)hexenoic acid as a colourless oil (410 mg, 50%); NMR: 1.7 (1H,m), 1.97 (1H,m), 2.3 (4H,m), 2.7 (1H,m), 3.82 (3H,s), 4.2 (2H,d), 5.35 (3H,m), 6.02 (1H,s), 6.9 (2H,m), 7.22 (2H,m), 7.45 (2H,m), 7.65 (2H,m) and 7.85 (1H,m).

EXAMPLES 2–5

Using a similar procedure to that described in Example 1, but starting from the appropriate 4-o-methoxyphenyl derivative of formula IV (R$^1$=methyl; Y=Z=H), the following acids of formula I (Y=Z=H) were obtained in yields of 29–73%:

| Example | X | m.p. (°C.) | Partial NMR Data |
| --- | --- | --- | --- |
| 2 | 2-Cl | 111–114* | 6.12 (1H,s), 6.9 (2H,m) 7.35 (5H,m), 7.87 (1H,m) |
| 3 | 3-Cl | oil | 5.7 (1H,s), 7.15 (9H,m). |
| 4 | 3-CN | 113–117 | 5.78 (1H,s), 6.89 (2H,m). 7.24 (2H,m), 7.12 (4H,m). 6.05 (1H,s), 6.95 (4H,m). |
| 5 | 2-CF$_3$ | oil | 7.6 (3H,m), 7.95 (1H,d). |

*melting point 125–126° C. after recrystallisation from ethyl acetate/hexane.

The required intermediates of formula IV (R$^1$=methyl were obtained in yields of 25–72%, using a similar procedure to that described for the analogous material in Example 1, but starting from the appropriately substituted benzaldehyde of formula VI:

| X | m.p. (°C.) | Partial NMR Data (ppm) |
| --- | --- | --- |
| 2-Cl | 147–150 | 6.02 (1H,s), 6.9 (2H,m) 7.32 (5H,m), 7.87 (1H,m) |
| 3-Cl | oil | 5.7 (1H,s), 6.9 (2H,m), 7.4 (6H,m) |
| 3-CN | oil | 5.75 (1H,s), 6.92 (2H,m), 7.22 (2H,m) 7.46 (2H,m), 7.63 (1H,m) 7.85 (2H,m) |
| 2-CF$_3$ | oil | 6.08 (1H,s), 7.17 (7H,m), 8.1 (1H,d) |

EXAMPLE 6 o-Chlorobenzaldehyde (260 mg) and p-toluene sulphonic acid (5 mg) were added to a solution of 4(Z)-6-(4-o-hydroxyphenyl-2,2-dimethyl-1,3-dioxan-cis-5-yl)hexenoic acid (B) (480 mg) in toluene (5 ml). The mixture was stirred for 3 hours. The product was isolated by flash column chromatography of the reaction mixture on silica, eluting with 1:19 (by volume) ethanol/methylene chloride, to give 4(Z)-6-([2,4,5-cis]-2-o-chlorophenyl-4-o-hydroxyphenyl-1,3-dioxan-5-yl)hexenoic acid (380 mg, 63%), m.p. 111°–114° C. (m.p. 125°–126° C. after recrystallisation from ethyl acetate/hexane); NMR: 1.82 (1H,m), 1.96 (1H,m), 2.36 (4H,m), 2.8 (1H,m), 4.2 (2H,m), 5.41 (3H,m), 6.12 (1H,s), 6.9 (2H,m), 7.35 (5H,m) and 7.87 (1H,m); m/e: 402 (M+).

The starting acid (B) was obtained as follows:

Sodium hydride (432 mg, 50% w/w dispersion in mineral oil) was added to a stirred solution of 4(Z)-6-(4-o-methoxyphenyl-2,2-dimethyl-1,3-dioxan-cis-5-yl)hexenoic acid (500 mg) in DMPU (7.5 ml) at 0°–5° C. After 5 minutes, ethanethiol (0.66 ml) was added dropwise during 3 minutes. The mixture was maintained at 0°–5° C. for 10 minutes and then heated at 135°–140° C. for 50 minutes. The cooled reaction mixture was diluted with water (15 ml) and then washed with dichloromethane (2×30 ml). The aqueous phase was acidified to pH 4 with acetic acid and extracted with diethyl ether (4×30 ml). The ether extracts were dried (MgSO$_4$) and evaporated. The oil obtained was purified by flash column chromatography on silica, eluting with 80:20:2 (by volume) toluene/ethyl acetate/acetic acid, to give 4(Z)-6-(4-o-hydroxyphenyl-2,2-dimethyl-1,3-dioxan-cis-5-yl)hexenoic acid, as a colourless solid (95 mg, 31%), m.p. 85°–89° C.; NMR: 1.6 (7H,m), 1.82 (1H,m), 2.32 (5H,m), 2.7 (1H,m), 3.83 (1H,dd), 4.12 (1H,qq), 5.24 (3H,m), 6.88 (3H,m), 7.17 (2H,m) and 8.47 (1H,s); m/e: 320 (M+).

EXAMPLES 7–18

Using a similar procedure to that described in Example 6, but starting from the appropriately substituted benzaldehyde of formula VI, the following acids of formula I (Y=Z=H) were obtained, in yields of 29–74%:

TABLE 5

| | Catches of diamondback moths | | | |
|---|---|---|---|---|
| | Weekly catch | | | |
| Composition of Lure | week 1 | week 2 | week 3 | week 4 |
| (Z)-11-hexadecenyl acetate (HLA) | 0 | 1 | 5 | 3 |
| HLA + Id | 87 | 379 | 332 | 197 |
| HLA + If | 171 | 369 | 287 | 126 |

EXAMPLE 19

A mixture containing 4(Z)-6-(4-[3-fluoro-2-hydroxyphenyl]-2,2-dimethyl-1,3-dioxan-cis-5-yl)hexenoic acid (340 mg), 2-chlorobenzaldehyde (170 mg), p-toluenesulphonic acid (2 mg) and dry toluene (2 ml) was stirred under an argon atmosphere for 3½ hours. The entire reaction mixture was then subjected to flash column chromatography, eluting with toluene/ethyl acetate/acetic acid (80:20:2 v/v), to give 4(Z)-6-([2,4,5-cis]-2-o-chlorophenyl-4-[3-fluoro-2-hydroxyphenyl]-1,3-dioxan-5-yl)hexenoic acid (295 mg) as a white foam; NMR: 2.2–2.9 (7H,m), 4.1–4.4 (2H,m), 5.2–5.6 (2H,m), 5.5 (1H,d,J=3 Hz), 6.1 (1H,s) and 6.7–7.9 (7H,m).

The starting material was obtained as follows:

(i) A mixture containing 3-fluorosalicylic acid (20 g) [obtained as white crystals, m.p. 145°–147° C., by the method of L N Ferguson et alia, J.Amer.Chem.Soc., 1950, 72, 5315], iodomethane (60 g), potassium carbonate (40 g) and acetone (200 ml) was heated under reflux for 24 hours. Water (500 ml) was added and the mixture was extracted with ether (3×150 ml). The combined extracts were dried (MgSO$_4$) and evaporated to give methyl 3-fluoro-2-methoxybenzoate (B) (21 g) as a yellow oil, which was used without further purification; NMR: 3.85 (3H,s), 3.95 (3H,s) and 6.8–7.6 (3H,m).

(ii) A solution containing B (15.9 g), potassium hydroxide (25 g) and water (5 ml) in methanol (200 ml) was stirred for 4 hours. The solvent was evaporated and the residue was dissolved in water (200 ml). The aqueous solution was washed with ether (100 ml) and acidified to pH 2 with concentrated hydrochloric acid. The white precipitate was collected by filtration and recrystallised from hexane to give 3-fluoro-2-methoxybenzoic acid (C) (14.2 g) as white crystals. [Further material (6.1 g) was obtained by extraction of the filtrate with ethyl acetate (100 ml).]

(iii) A solution of C (20 g) in thionyl chloride (25 ml) was heated under reflux for 3 hours. Excess thionyl chloride was removed by distillation and the residual oil was dissolved in toluene (25 ml). The solution was evaporated to give 3-fluoro-2-methoxybenzoyl chloride (D) as an oil, which was used without further purification.

(iv) A stirred solution of ethyl hydrogen 2-allylmalonate (20.3 g) in dry THF (200 ml) was treated with magnesium ethoxide (21.5 g) and the mixture was heated under reflux for 90 minutes. The mixture was cooled to 0° C. and a solution of D in dry THF (10 ml) was added at such a rate that the reaction temperature did not exceed 5° C. Stirring was continued for 1 hour and and the mixture was allowed to stand for 3 days. A saturated aqueous solution of ammonium chloride (150 ml) was added and the mixture extracted with ethyl acetate (3×100 ml). The combined extracts were washed with saturated brine (150 ml), dried (MgSO$_4$) and evaporated to give an oil which was purified by flash column chromatography, eluting with ethyl acetate/hexane (1:9 v/v) to give ethyl 2-allyl-3-(3-fluoro-2-methoxyphenyl)-3-oxo-propionate (E) (16.1 g), as a colourless oil; NMR: 1.2 (3H,t, J=7 Hz), 2.7 (2H,t,J=7 Hz), 4.0 (3H,d,J=3 Hz), 3.9–4.5 (3H,m), 4.8–5.3 (2H,m), 5.5–6.1 (1H,m) and 6.9–7.6 (3H,m).

(v) A solution of E (15.0 g) in dry THF (30 ml) was added with stirring and cooling to a suspension of lithium borohydride (3.0 g) in dry tetrahydrofuran (150 ml) at such a rate that the reaction temperature did not exceed 10° C. Stirring was continued for 15 hours at room temperature. The mixture was acidified to pH 2 by cautious addition of 2M hydrochloric acid with cooling. Water (100 ml) was then added. The mixture was extracted with ethyl acetate (3×200 ml). The combined extracts were washed with saturated brine (150 ml), dried (MgSO$_4$) and evaporated to give 2-allyl-1-(3-fluoro-2-methoxyphenyl)propane-1,3-diol (mainly cis-diol) as an oil (13.1 g). A solution of p-toluenesulphonic acid (5 mg) in 2,2-dimethoxypropane (100 ml) was added to this oil and the solution obtained was allowed to stand overnight. Triethylamine (3 drops) was added and the solvent was evaporated. The residue was purified by flash column chromatography, eluting with ethyl acetate/hexane (4:96 v/v), to give (4,5-cis)-5-allyl-4-(3-fluoro-2-methoxyphenyl)-2,2-dimethyl-1,3-dioxane (F) (4.95 g), as a colourless oil; NMR: 1.5 (3H,s), 1.55 (3H,s), 1.5–1.9 (1H,m), 2.2–2.5 (2H,m), 3.8 (1H,dd,J=11, 15 Hz), 3.95 (3H,d,J=3.3 Hz), 4.15 (1H,d m J=11 Hz), 4.85–5.05 (2H,m), 5.4 (1H,d,J=3 Hz), 5.4–5.7 (1H,m) and 6.9–7.3 (3H,m).

(vi) Ozone was passed through a solution of F (4,95 g) in ethyl acetate (200 ml.) at −78° C. until a permanent blue colour developed. The solution was flushed with argon until colourless. A solution of triphenylphosphine (5 g) in ethyl acetate (50 ml) was added. The mixture was allowed to warm to room temperature and allowed to stand for 24 hours. The solvent was evaporated and the residue purified by flash-column chromatography, eluting with chloroform, to give (4-[3-fluoro-2-methoxyphenyl]-2,2-dimethyl-1,3-dioxan-cis-5-yl)acetaldehyde (G) (4.5 g) as a colourless oil; NMR: 1.5 (3H,s), 1.55 (3H,s), 2.3 (1H, dd, J=12, 1.5 Hz), 2.45 (1H,m), 2.75 (1H,dd, J=18, 8 Hz), 4.0 (3H,d,J=3 Hz), 4.3 (1H,dm,J=12 Hz), 5.4 (1H,d,J=3 Hz), 6.9–7.4 (3H,m) and 9.55 (1H,s).

(vii) A solution of potassium t-butoxide (7.2 g) in dry THF (100 ml) was added to a stirred suspension of (3-carboxypropyl)triphenylphosphonium bromide (15.0 g) in dry THF (150 ml) at 0° C., under argon. The mixture was stirred for 30 minutes. Then a solution of G (4.5 g) in dry THF (50 ml) was added. After 1.5 hours, water (250 ml) was added and the volatile solvent was evaporated under reduced pressure. The aqueous solution washed with ethyl acetate, acidified to pH 5 with acetic acid and extracted with ethyl acetate. These extracts were washed with saturated brine, dried (MgSO$_4$) and evaporated. The oil obtained was purified by flash column chromatography, eluting with ethyl acetate/toluene/acetic and acid (20:80:2 v/v) to give 4(Z)-6-(4-[3-fluoro-2-methoxyphenyl]-2,2-dimethyl-1,3-dioxan-cis-5-yl)hexenoic acid (H) as an oil (4.1 g); NMR: 1.5 (3H,s), 1.55 (3H,s), 2.1–2.7 (7H,m), 3.8 (1H,dd,J=12, 1.5 Hz), 3.95 (3H,d,J=3 Hz), 4.15 (1H,dm,J=12 Hz), 5.1–5.5 (2H,m), 5.4(1H,d,J=3 Hz) and 6.9–7.3 (3H,m).

(viii) Ethane thiol (4.5 ml) was added to a stirred suspension of sodium hydride (2.9 g, 50% w/w dispersion in mineral oil) in DMPU (50 ml) at 0° C., under argon. After 30 minutes a solution of H (2.9 g) in DMPU (50 ml) was added. The mixture was heated at 140° C. for 3 hours, cooled and poured into ice-water (100 ml). The aqueous mixture was washed with dichloromethane (3×100 ml). The aqueous layer was acidified to pH 5 with acetic acid and extracted with ethyl acetate (3×100 ml). These extracts were washed with saturated brine (100 ml), dried (MgSO$_4$) and evaporated. The oil obtained was purified by flash column chromatography, eluting with ethyl acetate/toluene/acetic acid (50:50:2 v/v), to give 4(Z)-6-(4-[3-fluoro-2-hydroxyphenyl]-2,2-dimethyl-1,3-dioxan-cis-5-yl)hexenoic acid (2.05 g), as a colourless oil; NMR: 1.55 (3H,s), 1.6 (3H,s), 2.2–2.8 (7H,m), 3.8 (1H,dd,J=12,1.5 Hz), 4.1 (1H,dm,J=12 Hz), 5.1–5.5 (2H,m), 5.5 (1H,d,J=3 Jz) and 6.7–7.1 (3H,m).

EXAMPLE 20

A mixture of 2-chlorobenzaldehyde (100 mg), p-toluenesulphonic acid (2 mg) and 4(Z)-erythro-8-hydroxy-7-hydroxymethyl-8-o-hydroxyphenyl-4-octenoic acid (140 mg) was stirred in toluene (2 ml) for 20 hours. The reaction mixture was then purified by flash column chromatography on silica, eluting with 80:20:2 (by volume) hexane/ethyl acetate/acetic acid to give 4(Z)-6-([2,4,5-cis]-2-o-chlorophenyl-4-o-hydroxyphenyl-1,3-dioxan-5-yl)hexenoic (86 mg, 43%), m.p. 123°–125° C. with spectroscopic properties identical to those described in Example 6.

The starting acid was obtained as follows:

Sodium hydride (980 mg, 60% w/w dispersion in mineral oil) was added to a stirred suspension of 4(Z)-erythro-8-hydroxy-7-hydroxymethyl-8-o-methoxyphenyl-4-octenoic acid (A) (900 mg) in DMPU (35 ml) maintained at 0°–5° C. After 3 minutes, ethanethiol (1.5 ml) was added and the mixture was heated at 130° C. for 2 hours. The cooled mixture was diluted with water (40 ml) and washed with dichloromethane (2×45 ml). The aqueous phase was acidified to pH 4 with acetic acid and extracted with ether (4×45 ml). The extracts were dried (MgSO$_4$) and evaporated. The oil thus obtained was purified by flash chromatography on silica, eluting with 60:40:2 (by volume) toluene/ethyl acetate/acetic acid to give 4(Z)-erythro-8-hydroxy-7-hydroxymethyl-8-o-hydroxyphenyl-4-octenoic acid (785 mg, 92%) as a colourless oil; NMR; 1.2 (t, 2H), 1.83 (m, 1H), 2.44 (m, 6H), 3.73 (m, 3H), 4.5 (m, 2H), 5.3 (m, 3H) and 7.0 (m, 4H); m/e 280 (M$^+$).

The starting octenoic acid derivative A was itself obtained as follows:

(i) A solution of (4-o-methoxyphenyl-2,2-dimethyl-1,3-dioxan-cis-5-yl)acetaldehyde (15.8 g) in dry THF (75 ml) was added under argon to a stirred, ice-cooled solution of the ylid prepared from (3-carboxypropyl)triphenylphosphonium bromide (51.48 g) and potassium t-butoxide (26.88 g) in dry THF (400 ml). The mixture was stirred for 15 minutes at 4° C., then for 1.5 hours at ambient temperature and was then poured into ice-water (1 liter). The mixture obtained was washed with 50% v/v ether/hexane (2×250 ml) to remove the bulk of neutral material. The aqueous phase was acidified to pH 5 with acetic acid and extracted with ether (4×300 ml). These extracts were washed successively with water (3×150 ml), and saturated brine (2×100 ml), then dried (MgSO$_4$) and evaporated. The residue was purified by flash chromatography, eluting with toluene/ethyl acetate/acetic acid (80:20:2 v/v). The solid obtained was crystallised from 10% v/v ethyl acetate/hexane (250 ml) to give 4(Z)-6-(4-o-methoxyphenyl-2,2-dimethyl-1,3-dioxan-cis-5-yl)hexenoic acid (B) (13.0 g), m.p. 99°–101° C.; NMR: 1.52 (3H,s), 1.54 (1H,m), 1.56 (3H,s), 1.80 (1H,m), 2.28 (4H,m), 2.49 (1H,m), 3.77 (1H,dd J=11,1 Hz), 3.82 (3H,s), 4.16 (1H,dm J=11 Hz), 5.28 (2H,m), 5.45 (1H,d J=2 Hz), 6.83 (1H,dd J=7,1 Hz), 6.97 (1H,td J=7,1 Hz), 7.22 (1H,td J=8,1 Hz), 7.48 (1H,dm J=8 Hz).

(ii) A solution of B (4.20 g) in a mixture of water (12 ml), 2M hydrochloric acid (0.5 ml) and THF (40 ml) was heated with stirring at 60°–70° C. After 2 hours the mixture was cooled to ambient temperature and poured into water (100 ml). The aqueous mixture was extracted with ether (3×50 ml). The combined extracts were washed successively with water (2×40 ml) and saturated brine (40 ml), then dried (MgSO$_4$) and evaporated to give 4(Z)-erythro-8-hydroxy-7-hydroxymethyl-8-o-methoxyphenyl-4-octenoic acid as a colourless oil (3.80 g); NMR: 1.95 (1H,m), 2.11 (1H, m), 2.37 (5H,m), 3.67 (2H,m), 3.83 (3H,s), 4.84 (3H,br), 5.22 (1H,d J=4 Hz), 5.38 (2H,m), 6.88 (1H,br d J=7 Hz), 6.98 (1H,bt J=7 Hz), 7.25 (1H,td J=−7,1.5 Hz), 7.42 (1H,dd J=7,1.5 Hz).

EXAMPLE 21

Using a similar procedure to that described in Example 6, but starting from (−)-4(Z)-6-(4-o-hydroxyphenyl-2,2-dimethyl-1,3-dioxan-cis-5yl)hexenoic acid (A) there was obtained (−)-4(Z)-6-([2,4,5-cis]-2-o-chloro-phenyl-4-o-hydroxyphenyl-1,3-dioxan-5-yl)hexenoic acid in 64% yield as a solid, m.p. 32°–35° C.; $^{25}[\alpha]_D$ −119° (c 0.49; EtOAc), having an NMR essentially the same as that described for the racemic form in Example 6.

The necessary starting acid A was obtained as follows:

(i) Solid potassium t-butoxide (4.48 g) was added under argon to a stirred, ice-cooled mixture of (3-carboxypropyl)triphenylphosphonium bromide (6.44 g) and (−)-[2,3-trans]-tetrahydro-5-hydroxy-3-hydroxymethyl-2-o-methoxyphenylfuran (B) (2.24 g) in dry THF (75 ml). The mixture was stirred for 15 minutes at 4° C., then for 1 hour at ambient temperature and was then poured into ice-water (150 ml). The mixture obtained was washed with ether (2×50 ml) to remove the bulk of the neutral material. The aqueous phase was acidified to pH 4 with 1M hydrochloric acid and extracted with ether (1×100 ml, 2×50 ml). These combined extracts were washed successively with water (2×50 ml) and saturated brine (2×50 ml), then dried (MgSO$_4$) and evaporated. The residue was purified by flash chromatography, eluting with ether/hexane/acetic acid (80:20:1 v/v) to give (−)-erythro-4(Z)-8-hydroxy-7-hydroxymethyl-8-o-methoxyphenyl-4-octenoic acid (C) as a colourless oil (2.76 g); $^{22}[\alpha]_D$ −68.3° (c 1.1, methanol); NMR: 1.92 (1H,m), 2.0–2.6 (6H,m), 3.67 (2H,m), 3.82 (3H,s), 5.21 (1H,d J=5 Hz), 5.37 (2H,m), 6.87 (1H,dd J=8,1 Hz), 6.98 (1H,td J=7,1 Hz), 7.25 (1H,m), 7.42 (1H,dd J=7,1 Hz); m/e 294 (M+).

(ii) A solution of C (2.57 g) in 2,2-dimethoxypropane (8.5 ml) was treated with 'Amberlyst'-15 (Trademark of Rohm and Haas Company) strongly acid, macroreticular ion-exchange resin (0.5 g) and the mixture stirred for 2½ hours at ambient temperature. The solid was removed by filtration and washed with ether (10 ml). The filtrate and washings were concentrated in vacuo and the residue was purified by MPLC, eluting with hexane/ethyl acetate/acetic acid (80:20:1 v/v). A clear oil was obtained which slowly crystallised to give (−)-4(Z)-6-(4-o-methoxyphenyl-2,2-dimethyl-1,3-dioxan-cis-5-yl)hexenoic acid (D) (2.48 g). Recrystallisation from hexane gave solid of m.p. 71°–73° C., $^{23}[\alpha]_D$ −145.5° (c 1.1, methanol) with an NMR spectrum essentially the same as that of the corresponding racemate (Compound A in Ex. 1).

(iii) The hexenoic acid D was reacted with sodium thioethoxide in DMPU using the same procedure as described for the corresponding racemate in Example 6. There was thus obtained (−)-4-(Z)-6-(4-o-hydroxyphenyl-2,2-dimethyl-1,3-dioxan-cis-5-yl)hexenoic acid (A) in 94% yield as a colourless oil; $^{25}[\alpha]_D$ −128.6° (c 0.53; EtOAc), having an NMR spectrum essentially the same as that of the racemate described in Example 6.

The furan derivative B was itself obtained as follows:

(iv) Succinic anhydride (22 g), o-methoxybenzaldehyde (20 g) and anhydrous zinc chloride (44 g) were added to dichloromethane (dried over alumina, 200 ml) and the mixture stirred under argon. Triethylamine (41 ml) was added to the ice-cooled mixture over a period of 20 minutes. The reaction mixture was then stirred at 20°–25° C. for 18 hours, after which time hydrochloric acid (2M, 130 ml) and ethyl acetate (200 ml) were added. The subsequent mixture was stirred for 5 minutes. The aqueous phase was separated and extracted with ethyl acetate (150 ml) The combined extracts were washed with saturated brine (50 ml) and then extracted with saturated sodium bicarbonate solution (3×200 ml). The combined aqueous extracts were washed with ethyl acetate, and then acidified to pH 2 with concentrated hydrochloric acid. The oil which separated was extracted into ethyl acetate (2×150 ml). The combined extracts were washed with saturated brine (4×50 ml)until acid free, then dried (MgSO$_4$) and evaporated. Toluene (300 ml) was added to the residue and the mixture was distilled atmospheric pressure until the residual material attained 110° C. On cooling to 20° C., tetrahydro-2-o-methoxyphenyl-5-oxo-3-furancarboxylic acid separated as a crystalline white solid (27.2 g, 78%) (m.p. 106° C.) which was shown by NMR to be a mixture of [2,3-cis-]- and [2,3-trans]-isomer: 2.8–3.0 (2H,m), 3.1–3.6 (1H,m), 3.8 (3H,s), 5.82 (0.75 H,d) [trans], 5.95 (0.25 H,d) [cis], 6.8–7.5 (4H,m).

(v) A mixture of [2,3-cis-]- and [2,3-trans]-tetrahydro-2-o-methoxyphenyl-5-oxo-3-furancarboxylic acid (188.6 g) was added to an ice cooled solution of concentrated sulphuric acid (320 ml) in water (480 ml) and stirred at 20°–25° C. for 18 hours. Water (800 ml) was then added and the mixture extracted with ethyl acetate (2×750 ml). The combined extracts were washed with brine (4×500 ml) until acid free, dried (MgSO$_4$) and evaporated to low volume. Toluene (1 liter) was added and the distillation continued at atmospheric pressure until the residual material attained a temperature of 110° C. On cooling pure [2,3-trans]-tetrahydro-2-o-methoxyphenyl-5-oxo-3furancarboxylic acid separated as a white crystalline solid (169.5 g, 90%), m.p. 133°–134° C.; NMR: 2.8–3.0 (2H,d), 3.3–3.6 (1H,m), 3.8 (3H,s), 5.82 (1H,d), 6.8–7.4 (4H,m).

(vi) A solution of d-ephedrine (61.2 g) in hot ethyl acetate (150 ml) was added to a solution of [2,3-trans]-tetrahydro-2-o-methoxyphenyl-5-oxo-3-furancarboxylic acid (87.6 g) in hot ethyl acetate (350 ml). The mixture was allowed to cool to room temperature during 2 hours and the crystalline salt which had formed was separated by filtration to give 62 g of solid material having $^{25}[\alpha]_D$ +40.2° (methanol). This material was recrystallised twice from ethyl acetate to give 48 g of optically pure solid $^{25}[\alpha]_D$ +50.3° (methanol). This solid was added to ethyl acetate (1 liter) and 2M hydrochloric acid (150 ml). The ethyl acetate layer was washed with brine (2×100 ml) until the pH of the washings was pH 2–3, and then dried (MgSO$_4$) and evaporated. The residue was dissolved in boiling toluene (200 ml). Insoluble material was removed by hot filtration. The filtrate was allowed to cool to give (+)-[2,3-trans]-tetrahydro-2-o-methoxyphenyl-5-oxo-3-furancarboxylic acid (E) (27.4 g) $^{25}[\alpha]_D$ +33.0° (methanol). Recrystallisation from toluene gave material of $^{25}[\alpha]_D$ +33.8° (methanol), m.p. 125°–127° C. (decomposition), shown to be >98% optically pure by conversion of a small sample to its(−)-amyl ester and examination of the $^{13}$C NMR spectrum.

(vii) A solution of E (97.5 g) in dry tetrahydrofuran (150 ml) was cooled to 15° C. and treated with a solution of borane in tetrahydrofuran (500 ml of a 1M solution) with the temperature maintained at 20°–25° C. After 30 minutes the reaction was complete (as judged by TLC analysis) and water (200 ml) was added slowly to decompose the excess borane. The mixture was concentrated in vacuo and the residue was mixed with ethyl acetate (500 ml). The organic layer was washed successively with saturated potassium carbonate solution (2×100 ml) and saturated brine, dried (MgSO$_4$), and evaporated to give [4,5-trans]-tetrahydro-4-hydroxymethyl-5-o-methoxyphenylfuran-2-one (F) as a viscous oil (81.8 g), having $^{25}[\alpha]_D$ −14.2° (methanol) and a satisfactory NMR spectrum (d$_6$-acetone): 2.6 (3H,m), 3.7 (2H,m), 3.8 (3H,s), 4.1 (1H,br), 5.55 (1H,m), 6.8–7.5 (4H,m).

(viii) A solution of F (obtained above) in 1,2-dimethoxyethane (150 ml) and dry toluene (500 ml) was cooled under a nitrogen atmosphere to −60° C. A toluene solution of diisobutylaluminium hydride (672 ml of 1.23M solution) was then added slowly. After 30 minutes the reaction was quenched by addition of methanol (50 ml) and the mixture allowed to warm up to room temperature. 2M Hydrochloric acid (1 liter) and ethyl acetate (500 ml) were then added and the mixture stirred. The aqueous phase was separated and extracted with ethyl acetate (2×500 ml). The ethyl acetate phase and extracts were combined, dried (MgSO$_4$) and evaporated. The residual oil was dissolved in hot toluene (500 ml). The solution obtained gave on cooling (−)-[2,3-trans]-tetrahydro-5-hydroxy-3-hydroxymethyl-2-o- methoxyphenylfuran (B) as a white solid (63.3 g), $^{25}[\alpha]_D$ −24.2° (methanol), m.p. 110°–111° C.; NMR: 1.5–2.4 (3H,m), 3.4–4.0 (2H,m), 3.8 (3H,s), 4.2–4.8 (2H,br), 5.25 (1H, m), 5.6 (1H, m), 6.9–7.9 (4H, m).

EXAMPLES 22–23

Using a similar procedure to that described in Example 1 the following were obtained:

(Example 22): (−)-4(Z)-6-([2,4,5-cis]-2-o-cyanophenyl-4-o-hydroxyphenyl-1,3-dioxan-5-yl)hexenoic acid, in 74% yield as an oil, $^{25}[\alpha]_D$ −103.6° (c 2.58; EtOAc), starting from (−)-4(Z)-6-([2,4,5-cis]-2-o cyanophenyl-4-o-methoxyphenyl-1,3-dioxan-5-yl)hexenoic acid [itself obtained as an oil in 57% yield $^{25}[\alpha]_D$ −112.8° (c 0.454; EtOAc) starting from D in Example 21(ii), NMR essentially identical to that of the racemate, in an analogous manner to the corresponding starting material for Example 1]; and (Example 23): (−)-4(Z)-6-([2,4,5-cis]-2-p-cyanophenyl-4-o-hydroxyphenyl-1,3-dioxan-5-yl)hexenoic acid in 36% yield, as a solid, m.p. 53°–55° C.; $^{25}[\alpha]_D$ −132.5° (c 0.4; EtOAc), starting from (−)- 4(Z)-([2,4,5-cis]-2-p-cyanophenyl-4-o-methoxyphenyl-1,3-dioxan-5-yl)hexenoic acid [itself obtained as an oil in 49% yield, NMR: 1.65 (m, 1H) 2.0 (m, 1H), 2.30 (m, 4H), 2.54 (m, 1H), 3.83 (s, 3H), 4.18 (m, 2H), 5.31 (m, 3H), 5.77 (s, 1H), 6.91 (m, 2H), 7.27 (m, 1H), 7.53 (m, 1H) and 7.68 (s, 4H); m/e 420 (M+), starting from D in Example 21(ii), in an analogous manner to the corresponding starting material for Example 1].

EXAMPLE 24

A solution of sodium hydrogen carbonate (22 mg) in water (2.5 ml) was added to a stirred suspension of 4(Z)-6-([2,4,5-cis]-2-o-chlorophenyl-4-o-hydroxyphenyl-1,3-dioxan-5-yl)hexenoic acid (100 mg) in methanol (2.5 ml). After 30 minutes the mixture was evaporated to dryness in vacuo. Residual water was removed from the residue by azeotropic evaporation with toluene to give sodium 4(Z)-6-([2,4,5-cis]-2-o-chlorophenyl-4-o-hydroxyphenyl-1,3-dioxan-5-yl)hexenoate as a white solid (101 mg, 95%), m.p. 97°–100° C.

In a similar manner, but using potassium bicarbonate as starting material, the potassium salt m.p. (63°–65° C.) of 4(Z)-6-([2,4,5-cis]-2-o-chlorophenyl-4-o-hydroxyphenyl-1,3-dioxan-5-yl)hexenoic acid, was prepared.

EXAMPLE 25

Piperidine (43 mg) was added to a solution of 4(Z)-6-(2-o-chlorophenyl-4-o-hydroxyphenyl-1,3-dioxan-cis-5 yl)hexenoic acid (201 mg) in ethyl acetate (1 ml). The mixture was cooled to 0°–5° C. and hexane (5 ml) was added. The supernatant solvent was removed from the residual gum by decantation. Trituration of the gum with hexane gave a white solid which was crystallised from 1:1 (by volume) hexane and dichloromethane to give the piperidine salt of 4(Z)-6-([2,4,5-cis]-2-o-chlorophenyl-4-o-hydroxyphenyl-1,3-dioxan-5-yl)hexenoic acid as a white solid (111 mg, 46%), m.p. 68°–69° C.

EXAMPLE 26–28

Using a similar procedure to that described in Example 19 but starting from the appropriate 2,2-dimethyl-1,3-dioxane derivative of formula VII (Ra=Rb=methyl), the following compounds of formula I were obtained:

| Example | X | Y | Z | Yield (%) | m.p. (°C.) |
| --- | --- | --- | --- | --- | --- |
| 26 | 4-CN | H | F | 69 | 162–164 |
| 27 | 2-CN | H | F | 39 | 48–52 |
| 28 | 4-CN | F | H | 62 | 135–140 |

Partial NMR spectral data for the above compounds was as follows:

(Ex. 26): 5.40 (d J=2Hz, 1H, dioxane-C4-H), 5.75 (1H, s, dioxane-C2-H), 6.73–7.07 (m, 3 aromatic H), 7.70 (s, 4 aromatic H);

(Ex. 27): 5.45 (1H, d J=2Hz, dioxane-C4-H), 6.0 (1H, s, dioxane-C2-H), 6.66–6.93 (m, 3 aromatic H), 7.45–7.85 (4 aromatic H);

(Ex. 28): 5.45 (1H, d J=2Hz, dioxane-C4-H), 5.8 (1H s, dioxane-C2-H), 6.7–71 (m, 3 aromatic H), 7.70 (s, 4 aromatic H).

The starting material for Examples 26 and 27 was made as follows, by general analogy with that in Example 19:

(i) Triethylamine (42 ml) was added with stirring and cooling under an argon atmosphere to a solution containing 5-fluoro-2-methoxybenzaldehyde (23.1 g) [prepared as a white solid, m.p. 41°–43° C., by an analogous method to that described in U.S. Pat. Ser. No. 4,367,234] and anhydrous zinc chloride (45 g) in dry dichloromethane (250 ml) at such a rate that the reaction temperature did not exceed 25° C. Stirring was continued for 15 hours. The mixture was acidified to pH 2 with 2M hydrochloric acid and extracted with ethyl acetate (3×150 ml). The combined extracts were washed with saturated brine (6×100 ml) and extracted with a saturated solution of sodium hydrogen carbonate (4×60 ml). The combined aqueous extracts were washed with ethyl acetate (50 ml), acidified to pH 2 using concentrated hydrochloric acid, and extracted with ethyl acetate (4×100 ml). These extracts were washed with saturated brine (6×50 ml), dried (MgSO$_4$) and evaporated to give tetrahydro-2-(5-fluoro-2-methoxyphenyl)-5-oxo-3-furancarboxylic acid (40 g) as an oily mixture (A) of [2,3-cis] and [2,3-trans] diastereomers (39:61 by high pressure liquid chromatographic [HPLC] analysis); NMR: 2.93 (2H, d, J=8 Hz), 3.44 (1H, m), 3.88 (3H, s), 5.82 (1H, d, J=5,7 Hz) and 7.10 (3H, m). (ii) The diastereomeric mixture A (35 g) was added to a solution prepared from concentrated sulphuric acid (68 ml) and water (83 ml). The mixture was rapidly stirred for 72 hours. Water (160 ml) was added, with cooling, and the mixture was extracted with ethyl acetate (3×150 ml). The combined extracts were washed with saturated brine (6×100 ml), dried (MgSO$_4$) and evaporated to give tetrahydro-2-(5-fluoro-2-methoxy-phenyl)-5-oxo-3-furancarboxylic acid as a white solid (26.4 g; 14:86 [2,3-cis] to [2,3-trans]diastereomer by HPLC). Recrystallisation from toluene gave a further enrichment of the [2,3-trans] isomer (20.7 g; 8:92 cis: trans). This recrystallised material was added to a solution prepared from sulphuric acid (41 ml) and water (95 ml). The mixture was heated at 60° C. for 2.5 hours. Water (100 ml) was added and the mixture was extracted with ethyl acetate (3×100 ml). The combined extracts were washed with saturated brine (6×100 ml), dried (MgSO$_4$) and evaporated to give [2,3-trans]-tetrahydro-2-(5-fluoro-2-methoxyphenyl)-5-oxo-3-furancarboxylic acid as a white solid (B) (20 g; containing 2% w/w [2,3-cis]diastereomer by HPLC analysis).

(iii) A solution of borane-tetrahydrofuran complex (115 ml, 1M in tetrahydrofuran) was added to a stirred, ice-cooled solution of B (19.3 g) in dry THF (100 ml), under an atmosphere of argon. The mixture was allowed to warm to room temperature and stirring was continued for 15 hours. Water (40 ml) was added cautiously with cooling and the solvent was removed by evaporation. The residue was dissolved in ethyl acetate (100 ml). The solution obtained was washed successively with saturated potassium carbonate solution (20 ml) and saturated brine (50 ml), then dried (MgSO$_4$) and evaporated to give [4,5-trans]-tetrahydro-5-(5-fluoro-2-methoxyphenyl)-4-hydroxymethylfuran-2-one as an oil (C) (20.5 g); NMR: 2.5–2.8 (3H, m), 3.6–4.0 (5H, m), 5.57 (1H, d J=5.5 Hz) and 6.68–7.06 (3H, m).

(iv) A solution of diisobutylaluminium hydride (114 ml, 1.5M in toluene) was added over 45 minutes to a stirred mixture containing C (20.2 g), dry toluene (90 ml) and dry 1,2-dimethoxyethane (22 ml) at −70° C. under argon. Stirring was continued for 2 hours. Methanol (3 ml) was then added and the mixture was allowed to warm to room temperature. Saturated brine (120 ml) and ethyl acetate (300 ml) were added. Insoluble material was removed by filtration. The organic layer was separated and the aqueous layer was extracted with ethyl acetate (100 ml). The combined ethyl acetate fractions were washed with saturated brine (2×100 ml), dried (MgSO$_4$), and evaporated. The residual oil was purified by flash chromatography, eluting with petroleum ether (b.p. 40°–60° C.)/ethyl acetate (1:4 v/v), to give [2,3-trans]-tetrahydro-2-(5-fluoro-2-methoxyphenyl)-5-hydroxy-3-hydroxymethyl-furan as a white solid (D) (9.2 g); NMR: 1.75–2.45 (3H, m), 3.65–4.05 (2H, m), 3.85 (3H, s), 4.45 (1H, t J=4 Hz), 5.25 (1H, d J=3 Hz), 5.65 (2H, br s) and 6.86–7.23 (3H, m).

(v) A mixture containing (3-carboxypropyl)-triphenylphosphonium bromide (49.8 g), potassium t-butoxide (26.0 g) and dry toluene (300 ml) was stirred at 80° C. for 30 minutes under argon, and allowed to cool to room temperature. A solution of D (7.0 g) in dry tetrahydrofuran (40 ml) was added and stirring was continued for 1 hour. Water (140 ml) was added, with ice-water cooling, and the mixture was washed with ethyl acetate (3×60 ml). The aqueous phase was acidified to pH 5 with oxalic acid and extracted with ethyl acetate (3×100 ml). These extracts were combined, solid material removed by filtration and the filtrate evaporated. The residue was mixed with ether (100 ml) and residual solid removed by filtration. This filtrate was then extracted with a saturated solution of sodium hydrogen carbonate (3×100 ml). The combined extracts were washed with ethyl acetate (100 ml). The aqueous phase was then acidified to pH 5 with oxalic acid and extracted with ethyl acetate (3×100 ml). These combined extracts were washed with saturated brine (150 ml), dried (MgSO$_4$) and evaporated to give erythro-4(Z)-8-hydroxy-7-hydroxymethyl-8-(5-fluoro-2-methoxy-phenyl)octenoic acid as an oil (E) (9.0 g); NMR: 1.8–2.6 (7H, m), 3.75 (2H, m), 3.78 (3H, s), 5.2–5.5 (3H, m), 6.2 (3H, br s) and 6.7–7.3 (3H, m).

(vi) A mixture of E (6.3 g), p-toluenesulphonic acid (5 mg) and 2,2-dimethoxypropane (40 ml) was allowed to stand for 16 hours at ambient temperature. Triethylamine (3 drops) was added and the solvent was evaporated. The residual oil was purified by flash chromatography, eluting with toluene/ethyl acetate/acetic acid (85:15:2 v/v), to give 4(Z)-6-(4-[5-fluoro-2-methoxyphenyl]-2,2-dimethyl-1,3-dioxan-cis-5-yl)hexenoic acid as a colourless oil (F) (6.4 g); NMR: 1.45 (3H, s), 1.48 (3H, s), 1.6–2.5 (7H, m), 3.74 (3H, s), 3.62–3.78 (1H, dm, J=11 Hz), 4.02–4.13 (1H, dm J=11 Hz), 5.05–5.38 (2H, m), 5.3 (1H, d J=3 Hz) and 6.6–7.15 (3H, m).

(vii) Ethanethiol (4.4 ml) was added to a stirred suspension of sodium hydride (2.62 g, 50% w/w dispersion in mineral oil) in DMPU (80 ml) at 0° C. under argon. After 1 hour, the mixture was heated to 85° C. and then cooled to ambient temperature. A solution of F (3.52 g) in DMPU (20 ml) was added and the mixture was heated at 85° C. for 2 hours. The cooled mixture was poured into ice-water (160 ml) and extracted with dichloromethane (2×100 ml). The aqueous layer was acidified to pH 3 with 2M hydrochloric acid and extracted with ether (3×150 ml). The combined extracts were washed successively with water (2×100 ml) and saturated brine (100 ml), then dried (MgSO$_4$) and evaporated. The residual oil was purified by flash chromatography, eluting with toluene/ethyl acetate/acetic acid (80:20:2 v/v), to give 4(Z)-6-(4-[5-fluoro-2-hydroxyphenyl]-2,2-dimethyl-1,3-dioxan-cis-5-yl)hexenoic acid as a colourless oil (2.62 g); NMR: 1.5 (3H, s), 1.55 (3H, s), 2.2–2.8 (7H, m), 3.8 (1H, dd J=12, 1.5 Hz), 4.1 (1H, dm J=12 Hz), 5.1–5.6 (2H, m), 5.4 (1H, d J=3 Hz) and 6.7–7.3 (3H, m).

EXAMPLE 29

Using a similar Wittig procedure to that described in part (i) of Example 20 but starting from ([2,4,5-cis]-2-o-chlorophenyl-4-o-hydroxyphenyl-1,3-dioxan-5-yl)acetaldehyde and the ylid prepared from (3-carboxypropyl)triphenylphosphonium bromide and potassium t-butoxide, 4(Z)-6-([2,4,5-cis]-2-o-chlorophenyl-4-o-hydroxyphenyl-1,3-dioxan-5-yl)hexenoic acid may be obtained in 23% yield, essentially identical to that isolated in Example 20, 6 and 2.

The starting acetaldehyde derivative was obtained as follows:

(a) A solution of [4,5-cis]-5-allyl-4-o-methoxyphenyl-2,2-dimethyl-1,3-dioxane (7.86 g) in dry THF (10 ml) was treated at 4° C. under argon with a solution of lithium diphenylphosphide prepared from chlorophenylphosphine (16.60 g) and lithium metal (2.1 g) in dry THF (75 ml). The mixture was stirred for 0.5 hours at 4° C., then for 3.5 hours at 50° C., cooled to 10° C. and poured into an ice-water mixture (500 ml). The aqueous mixture was acidified with acetic acid and extracted with ether (3×200 ml). The combined extracts were washed with water (3×100 ml), then with saturated brine (2×100 ml), dried (MgSO$_4$) and the solvent evaporated. The oil obtained was purified by flash chromatography, eluting with 12.5% v/v ethyl acetate/hexane, to give [4,5-cis]-5-allyl-4-o-hydroxyphenyl-2,2-dimethyl-1,3-dioxane as a solid (7.20 g), m.p. 49°–51° C., having a satisfactory NMR spectrum.

(b) A solution of 2-chlorobenzaldehyde (1 ml), p-toluenesulphonic acid (20 mg) and [4,5-cis]-5-allyl-2,2-dimethyl-4-o-hydroxyphenyl-1,3-dioxane (500 mg) was stirred in toluene (1 ml) for 2 hours under argon. Ether (50 ml) was added and the whole mixture washed with 0.5M sodium hydroxide solution (2×25 ml). The ether layer was then further washed with saturated brine (3×40 ml), dried (MgSO$_4$) and evaporated. The residue was purified by flash column chromatography on silica. Elution with 12% (v/v) ethyl acetate/hexane gave [2,4,5-cis]-5-allyl-2-o-chlorophenyl-4-o-hydroxyphenyl-1,3-dioxane as a colourless solid, m.p. 87°–89° C. (494 mg; 74.5%); NMR: 1.85 (m,1H), 2.15 (m,1H), 2.68

(m,1H), 4.26 (m,2H), 5.07 (m,2H), 5.50 (d,1H), 5.68 (m,1H), 6.06 (s,1H) 7.10 (m,7H) and 7.72 (m,2H).

(c) Ozone was passed through a solution of [2,4,5-cis]-5-allyl-2-o-chlorophenyl-4-o-hydroxyphenyl-1,3-dioxane (370 mg) in methylene chloride (35 ml) at −78° C. until a permanent blue colour developed. The solution was flushed with argon until colourless and triphenyl phosphine (390 mg) was added. The mixture was allowed to reach room temperature and purified by flash column chromatography on silica. Elution with 30% (v/v) ethyl acetate/hexane gave ([2,4,5-cis]-2-o-chlorophenyl-4-o-hydroxyphenyl-1,3-dioxan-5-yl)acetaldehyde as a colourless oil (167 mg; 45%); NMR: 2.62 (m,2H), 3.15(m,1H), 4.28 (m,2H), 5.47 (d,1H), 6.05 (s,1H), 7.43 (m,8H) and 9.70 (s,1H); m/e 333 (M++H).

EXAMPLE 30

Using a similar procedure to that described in Example 20, the sodium salt, m.p. 65°–69° C., and the potassium salt, m.p. 96°–98° C. (hygroscopic) of (−)-4(Z)-6-([2,4,5-cis]-2-o-chlorophenyl-4-o-hydroxyphenyl-1,3-dioxan-5-yl)hexenoic acid, were prepared using sodium and potassium bicarbonate, respectively.

EXAMPLE 31

Illustrative pharmaceutical dosage forms of the invention include the following tablet, capsule, and aerosol formulations, which may be obtained by conventional procedures well known in the art of pharmacy and are suitable for therapeutic or prophylactic use in humans:

| (a) Tablet I | mg/tablet |
|---|---|
| Compound X* | 1.0 |
| Compound Y* | 1.0 |
| Lactose Ph. Eur. | 92.25 |
| Croscarmellose sodium | 4.0 |
| Maize starch paste (5% w/v aqueous paste) | 0.75 |
| Magnesium stearate | 1.0 |
| (b) Tablet II | mg/tablet |
| Compound X* | 5 |
| Compound Y* | 50 |
| Lactose Ph. Eur. | 218.75 |
| Croscarmellose sodium | 6.0 |
| Maize starch | 15.0 |
| Polyvinylpyrrolidone (5% w/v aqueous paste) | 2.25 |
| Magnesium stearate | 3.0 |
| (c) Tablet III | mg/tablet |
| Compound X* | 25 |
| Compound Y* | 75 |
| Lactose Ph. Eur. | 182.75 |
| Croscarmellose sodium | 12.0 |
| Maize starch paste (5% w/v aqueous paste) | 2.25 |
| Magnesium stearate | 3.0 |
| (d) Capsule I | mg/capsule |
| Compound X* | 5 |
| Compound Y* | 5 |
| Lactose Ph. Eur. | 488.5 |
| Magnesium stearate | 1.5 |
| (e) Capsule II | mg/capsule |
| Compound X* | 50 |
| Compound Y* | 250 |
| Lactose Ph. Eur. | 199 |
| Magnesium Stearate | 1 |
| (f) Aerosol I | mg/ml |
| Compound X* | 5.0 |
| Compound Y* | 5.0 |
| Sorbitan trioleate | 13.5 |
| Trichlorofluoromethane | 910.0 |
| Dichlorodifluoromethane | 490.0 |
| (g) Aerosol II | mg/ml |
| Compound X* | 0.1 |
| Compound Y* | 0.1 |
| Sorbitan trioleate | 0.27 |
| Trichlorofluoromethane | 70.0 |
| Dichlorodifluoromethane | 280.0 |
| Dichlorotetrafluoroethane | 1094.0 |
| (h) Aerosol III | mg/ml |
| Compound X* | 1.0 |
| Compound Y* | 2.0 |
| Sorbitan trioleate | 3.38 |
| Trichlorofluoromethane | 67.0 |
| Dichlorodifluoromethane | 1086.0 |
| Dichlorotetrafluoroethane | 191.6 |
| (i) Aerosol IV | mg/ml |
| Compound X* | 1.5 |
| Compound Y* | 2.0 |
| Soya lecithin | 2.7 |
| Trichlorofluoromethane | 67.5 |
| Dichlorodifluoromethane | 1085.0 |
| Dichlorotetrafluoroethane | 191.6 |

Note
*Compound X is a compound of formula I, or a pharmaceutically acceptable salt thereof defined herein, for example a compound of formula I described in any preceding Examples, typically Example 1, 2, 6, 13 or 20.
*Compound Y is a $TXA_2$ synthetase inhibitor, or a pharmaceutically acceptable salt thereof, for example as specified hereinbefore e.g. dazoxiben, or the compound known as CV4151, or a salt thereof.

The tablet compositions (a)–(c) may be enteric coated by conventional means, for example to provide a coating of cellulose acetate phthalate. The aerosol compositions (f)–(i) may be used in conjuction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid. Other formulations containing different amounts of the active ingredients X and Y may be obtained using generally analogous procedures and exipients well known in the pharmaceutical art.

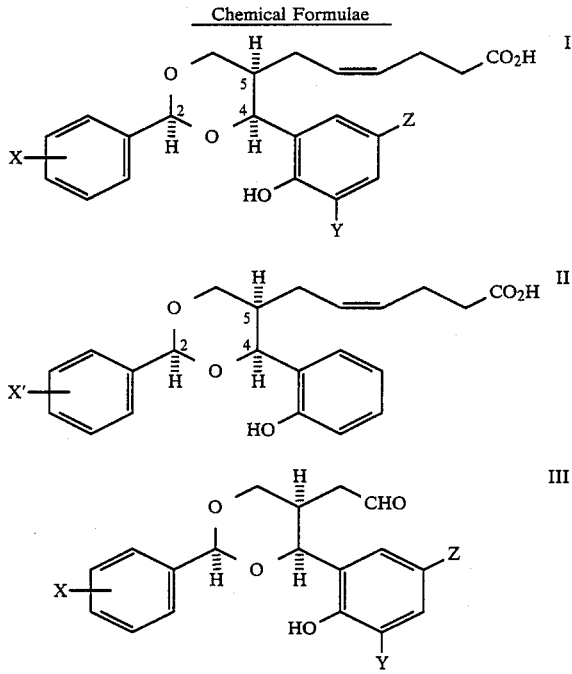

Chemical Formulae

Chemical Formulae
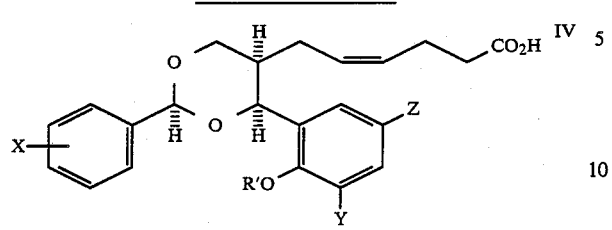   IV
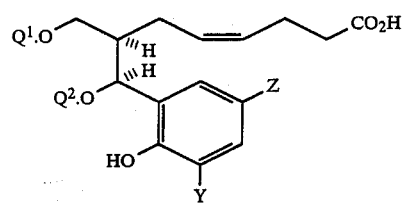   V
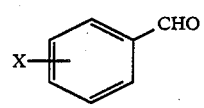   VI
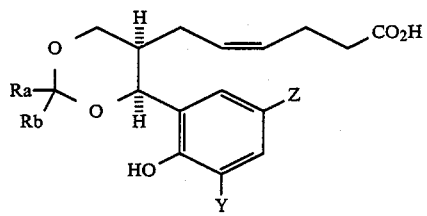   VII
Scheme 1
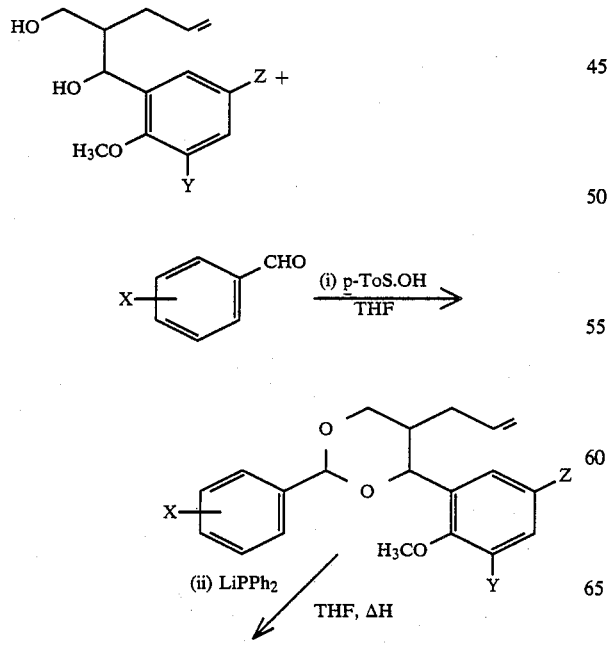
Scheme 1 -continued
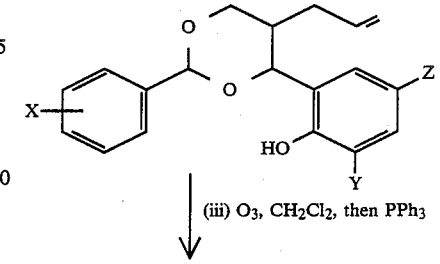
(iii) O₃, CH₂Cl₂, then PPh₃
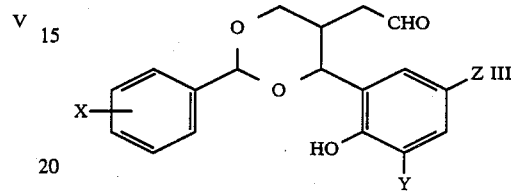   III
Tos = p-toluenesulphonyl
Ph = phenyl
TxA₂ Synthetase Inhibitors
Sheet A
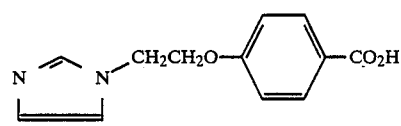   1
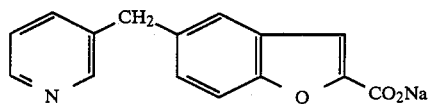   2
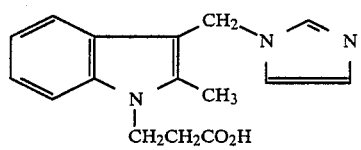   3
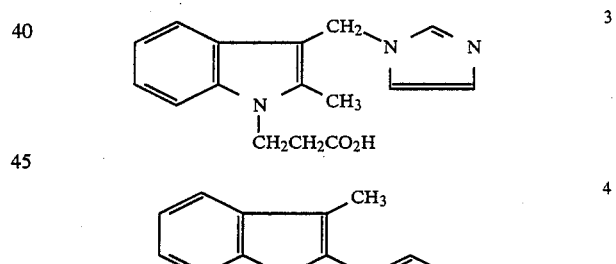   4
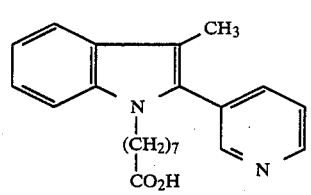   5
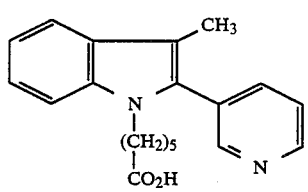   6

-continued
TxA₂ Synthetase Inhibitors

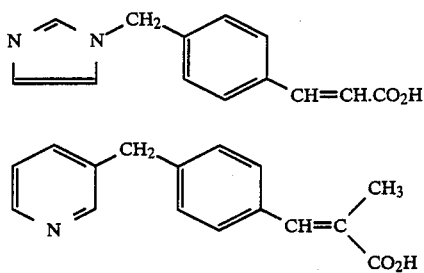

7

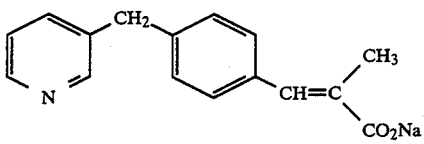

Sheet B

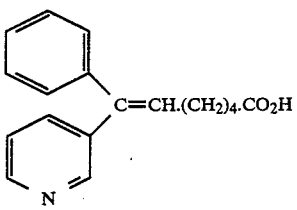

9

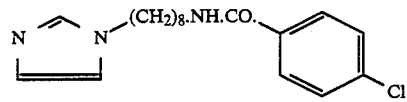

10

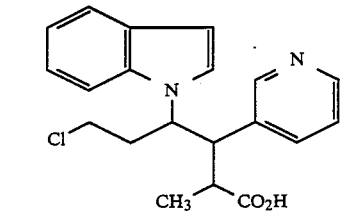

11

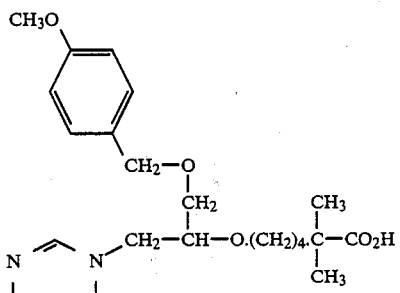

12

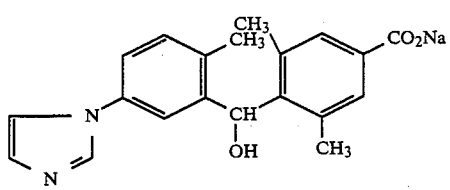

13

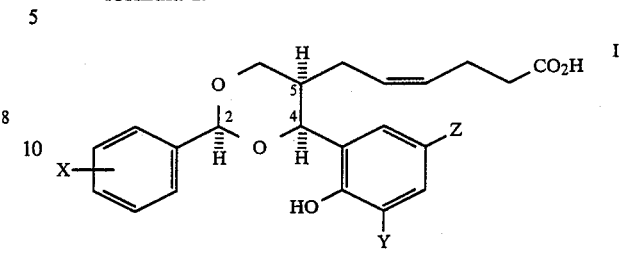

14

What is claimed is:

1. A pharmaceutical composition for use in a disease or medical condition in which thromboxane A₂ and/or a related prostanoid constrictor substance is involved which comprises as active ingredients:

(i) an effective amount of 1,3-dioxane ether of the formula I:

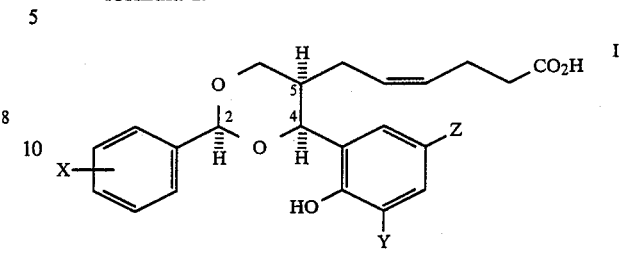

wherein X is selected from fluoro, chloro, bromo, trifluoromethyl, cyano, methoxy and nitro; and one of Y and Z is hydrogen or fluoro, and the other is hydrogen; and wherein the groups at positions 2, 4 and 5 of the dioxane ring have cis-relative stereochemistry; or a pharmaceutically acceptable salt thereof; and (ii) an effective amount of inhibitor of the synthesis of thromboxane A₂ selected from the group consisting of:

(1) 4-[2-(1H-imidazol-1-yl)ethoxy]benzoic acid (dazoxiben), (2) sodium 5-(3-pyridylmethyl)benzofuran-2-carboxylic acid (furegrelate), (3) 3-[3-(1H-imidazol-1-ylmethyl)-2-methyl-1H-indol-1-yl]propanoic acid (UK38485), (4) 8-[3-methyl-2-(3-pyridyl)-1H-indol-1-yl]octanoic acid (CGS12970), (5) 5-(5-carboxypentyl)imidazo[1,5-a]pyridine (CGS13080), (6) 6-[5-chloro-3-methyl-2-(3-pyridyl)-1H-indol-1-yl]hexanoic acid (CGS14854), (7) (E)-4-(1-imidazolylmethyl)cinnamic acid (OKY046), (8) sodium (E)-3-[4-(3-pyridylmethyl)phenyl]methacrylate (OKY1580), (9) (E)-3-[4-(3-pyridylmethyl)phenyl]methacrylic acid hydrochloride (OKY1581),

(10) (E)-7-phenyl-7-(3-pyridyl)-6-heptenoic acid (CV4151),

(11) N-[(1H)-imidazol-1-yl)octyl]-4-chlorobenzamide,

(12) 1-(3-benzloxy-1(E)-octenyl)imidazole (CBS645),

(13) 2,2-dimethyl-6-[2-(1H-imidazol-1-yl)-1-([4-methoxyphenyl]methoxymethyl)-ethoxy]hexanoic acid (SC41156),

(14) sodium 4-[alpha-hydroxy-5-(1H-imidazol-1-yl)-2-methylbenzyl]-3,5-dimethyl-benzoate (Y20811); having the formulae set out hereinbefore; and the pharmaceutically acceptable salts thereof or, in the case of inhibitor (2), (8), (9) and (14), the salt free form thereof;

together with a pharmaceutically acceptable diluent or carrier.

2. A composition as claimed in claim 1 wherein, in the active ingredient (i), X is selected from 2-fluoro, 2-chloro, 2-bromo, 2-cyano, 2-trifluoromethyl, 3-fluoro, 3-chloro, 3-cyano, 3-nitro, 3-methoxy, 4-chloro, 4-cyano, 4-nitro and 4-methoxy; Y is hydrogen or fluoro; and Z is hydrogen.

3. A composition as claimed in claim 1 wherein, in the active ingredient (i), X is selected from 2-chloro, 3- chloro, 2-cyano, 4-cyano, 3-nitro and 4-nitro; Y and Z are hydrogen.

4. A composition as claimed in claim 1 wherein the active ingredient (i) is selected from 4(Z)-6-([2,4,5-cis]-2-o-cyanophenyl-4-o-hydroxyphenyl-1,3-dioxan-5-yl)hexenoic acid, 4(Z)-6-([2,4,5-cis]-2-o-chlorophenyl-4-o-hydroxyphenyl-1,3-dioxan-5-yl)hexenoic acid, 4(Z)-6-([2,4,5-cis]-2-p-cyanophenyl-4-o-hydroxphenyl-1,3-dioxan-5-yl)hexenoic acid, and the pharmaceutically acceptable salts thereof.

5. A composition as claimed in claim 1 wherein the active ingredient (i) is present as a pharmaceutically acceptable salt selected from alkali metal and alkaline earth metal salts, aluminium and ammonium salts, and from salts with organic amines and quaternary bases forming physiologically acceptable cations.

6. A composition as claimed in claim 1 or 4 wherein the active ingredient (ii) is selected from the known inhibitors of thromboxane $A_2$ synthesis, dazoxiben, CV 4151, and the pharmaceutically acceptable salts thereof.

7. A composition as claimed in claim 1 which comprises as active ingredient (i), 4(Z)-6-([2,4,5-cis]-2-o-chlorophenyl-4-o-chlorophenyl-4-o-hydroxyphenyl-1,3-dioxan-5-yl)hexenoic acid, or a pharmaceutically acceptable salt thereof; and as active ingredient (ii), the known inhibitor of thromboxane $A_2$ synthesis, dazoxiben, CV4151, or a pharmaceutically acceptable salt thereof.

8. A method of medical treatment or prophylaxis of a disease or medical condition in which thromboxane $A_2$ and/or a related prostanoid constrictor substance is involved in a warm-blooded animal requiring such treatment, which comprises administering to said animal a therapeutically or prophylactically effective amount of an agent (i) comprising a compound of the formula I, or a pharmaceutically acceptable salt thereof, as defined in claim 7 and a therapeutically or prophylactically effective amount of an agent (ii) comprising an inhibitor of thromboxane $A_2$ synthesis, as defined in claim 1.

9. A method as claimed in claim 8 wherein the agent (i) is selected from:
4(Z)-6-([2,4,5-cis]-2-o-cyanophenyl-4-o-hydroxyphenyl-1,3-dioxan-5-yl)hexenoic acid,
4(Z)-6-([2,4,5-cis]-2-o-chlorophenyl-4-o-hydroxyphenyl-1,3-dioxan-5-yl)hexenoic acid,
4(Z)-6-([2,4,5-cis]-2-p-cyanophenyl-4-o-hydroxphenyl-1,3-dioxan-5-yl)hexenoic acid, and the pharmaceutically acceptable salts thereof.

10. A method as claimed in claim 8 wherein ingredient (i) is selected from:
4(Z)-6-([2,4,5-cis]-2-o-chlorophenyl-4-o-hydroxyphenyl-1,3-dioxan-5-yl)hexenoic acid and the pharmaceutically acceptable salts thereof.

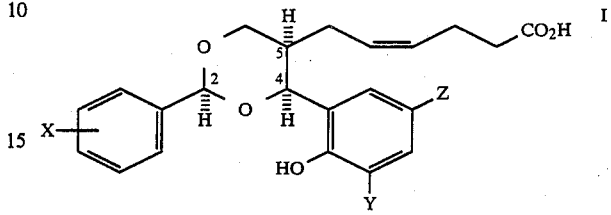

11. A composition as claimed in claim 1 which comprises, as active ingredient (i), 4(Z)-6-([2,4,5-cis]-2-o-chlorophenyl-4-o-chlorophenyl-4-o-hydroxyphenyl-1,3-dioxan-5-yl)hexenoic acid, or a pharmaceutically acceptable salt thereof; and, as active ingredient (ii), an effective amount of the inhibitor 3-[3-(1H-imidazol-1-ylmethyl)-2-methyl-1H-indolyl]propanoic acid (UK38485), or a pharmaceutically acceptable salt thereof.

12. A method as claimed in claim 9 wherein the agent (i) and the agent (ii) are administered to said animal separately.

13. A method as claimed in claim 9 or 12 wherein the agent (i) is selected from the group consisting of
4(Z)-6-([2,4,5-cis]-2-o-chlorophenyl-4-o-hydroxyphenyl-1,3-dioxan-5-yl)hexenoic acid, and the pharmaceutically acceptable salts thereof; and the agent (ii) is selected from the group consisting of
4-[2-(1H-imidazol-1-yl)ethoxy]benzoic acid (dazoxiben), (E)-7-phenyl-7-(3-pyridyl)-6-heptenoic acid (CV4151), and the pharmaceutically acceptable salts thereof.

14. A method as claimed in claim 9 or 12 wherein the agent (i) is selected from the group consisting of
4(Z)-6-([2,4,5-cis]-2-o-chlorophenyl-4-o-hydroxyphenyl-1,3-dioxan-5-yl)hexenoic acid, and the pharmaceutically acceptable salts thereof; and the agent (ii) is selected from the group consisting of
3-[3-(1H-imidazol-1-ylmethyl)-2-methyl-1H-indol-1-yl]propanoic acid (UK38485), and the pharmaceutically acceptable salts thereof.

* * * * *